United States Patent [19]

Cretenot et al.

[11] Patent Number: 4,906,717

[45] Date of Patent: Mar. 6, 1990

[54] HYDROABSORBENT RESINS, PRODUCTION METHOD AND APPLICATION THEREOF FOR OBTAINING ARTICLES CAPABLE OF ABSORBING AQUEOUS FLUIDS

[75] Inventors: Claude-Lise Cretenot, Verneuil en Hal; Bernard Wiegert, Rieux, both of France

[73] Assignee: Societe Chimique Des Charbonnages S.A., France

[21] Appl. No.: 157,108

[22] Filed: Feb. 10, 1988

Related U.S. Application Data

[63] Continuation of Ser. No. 905,341, filed as PCT FR85/00372 on Dec. 24, 1985, published as WO86/04070 on Jul. 17, 1986, abandoned.

[30] Foreign Application Priority Data

Dec. 27, 1984 [FR] France ................. 84 19878

[51] Int. Cl.$^4$ ........................... C08F 220/36
[52] U.S. Cl. .................................. 526/312
[58] Field of Search ............. 526/209, 240, 312

[56] References Cited

U.S. PATENT DOCUMENTS

| | | | |
|---|---|---|---|
| 3,634,366 | 1/1972 | Chujo et al. ............. | 526/258 |
| 4,212,782 | 7/1980 | Klein ........................ | 525/113 |
| 4,460,568 | 7/1984 | Strasilla et al. ......... | 526/312 |
| 4,486,489 | 12/1984 | George ..................... | 526/312 |
| 4,581,402 | 12/1986 | Dunk et al. .............. | 526/312 |

FOREIGN PATENT DOCUMENTS 8100764 of 1981 PCT Int'l Appl. .

*Primary Examiner*—Joseph L. Schofer
*Assistant Examiner*—Peter F. Kulkosky
*Attorney, Agent, or Firm*—Finnegan, Henderson, Farabow, Garrett & Dunner

[57] ABSTRACT

Water-absorbing resin based on acrylic acid and on dialkylaminoalkyl acrylate.

It comprises from 40 to 60% on a molar basis of acrylic acid, at least partially in salt form if appropriate, and from 60 to 40% on a molar basis of at least one dialkylaminoalkyl acrylate, at least partially in salt form or quaternized if appropriate. It is manufactured by copolymerization either in aqueous solution or in an inverse emulsion, in the presence of at least one free-radical generator.

Application to the production of articles capable of absorbing aqueous liquids.

6 Claims, No Drawings

HYDROABSORBENT RESINS, PRODUCTION METHOD AND APPLICATION THEREOF FOR OBTAINING ARTICLES CAPABLE OF ABSORBING AQUEOUS FLUIDS

This is a continuation of application Serial No. 905,341, filed as PCT FR85/00372 on Dec. 24, 1985, published as WO86/04070 on July 17, 1986, now abandoned.

The present invention relates to water-absorbing resins, the process for their manufacture and their application to the production of articles capable of absorbing aqueous liquids.

European Patent No. 055,728 discloses copolymers having a high capacity for absorbing and retaining water, and comprising:

(a) from 65 to 95% by weight of acrylic acid, and (b) from 5 to 35% by weight of a monomer chosen from alkyl methacrylates in which the alkyl group contains from 1 to 30 carbon atoms, cyclohexyl methacrylate, phenyl acrylate, phenoxyalkyl acrylates in which the alkyl group contains from 2 to 6 carbon atoms, and dialkylaminoalkyl (meth)acrylates in which the alkyl group contains from 2 to 6 carbon atoms and in which the dialkyl group contains from 2 to 8 carbon atoms.

These copolymers, in which the preferred monomer is lauryl methacrylate, 2-hydroxyethyl methacrylate or phenoxyethyl acrylate, may comprise a crosslinking agent.

U.S. Pat. No. 3,634,366 discloses a polymerization process, in the absence of any initiator and under an inert atmosphere:

of a monomer chosen from α,β-unsaturated monobasic and dibasic aliphatic acids, it being possible for this monomer to be acrylic acid, and of an unsaturated monomer containing a tertiary amino group and capable of quaternization, it being possible for this monomer to be chosen from a group comprising dimethylaminomethyl methacrylate or dimethylaminoethyl methacrylate.

According to this document, the molar ratio of the acid monomer to the unsaturated amino monomer is between 0.8 and 1.2; the polymerization is carried out for a period of 1 to 10 hours and at a temperature of 0° to 150° C. The products obtained are useful as soil conditioners and flocculating agents.

U.S. Pat. No. 4,212,782 also discloses a water-soluble polymer, amphoteric in aqueous medium, of a water-soluble salt of methacrylic acid and of a 2-monoalkylaminoethyl methacrylate in which the alkyl group has not more than 6 carbon atoms, the molar ratio of the two monomers being between 2:3 and 3:2.

The aim of the present invention lies in the development of products having a very high capacity for absorbing and retaining water, pure or saline, that is to say containing a significant quantity of inorganic ions. The present invention is based on the surprising finding that:

the teaching of European Patent No. 055,728, namely, the nature of the preferred monomer and the proportion of acrylic acid of between 65 and 95% by weight, does not make it possible to solve the problem of a high capacity for absorbing and retaining pure or saline water;

a copolymer of acrylic acid and dimethylaminoethyl methacrylate such as described in U.S. Pat. No. 3,634,366 has no capacity for absorbing and retaining pure or saline water;

a copolymer of methacrylic acid and methylaminoethyl acrylate such as described in U.S. Pat. No. 4,212,782 has only a weak capacity for absorbing and retaining pure or saline water.

Consequently, a first subject of the present invention is a water-absorbing resin characterized in that it comprises from 40 to 60% on a molar basis of acrylic acid, at least partially in salt form if appropriate, and from 60 to 40% on a molar basis of at least one dialkylaminoalkyl acrylate in which each alkyl group contains from 1 to 4 carbon atoms, at least partially in salt form or quaternized if appropriate.

Acrylic acid which is at least partially in salt form if appropriate means that the acrylic acid may be partly replaced by at least one of its ammonium or alkali metal or alkaline earth metal salts. Dialkylaminoalkyl acrylate at least partially in salt form or quaternized if appropriate means that the said dialkylaminoalkyl acrylate may be partly replaced by at least one of its salts, such as its quaternary ammonium salt.

The water-absorbing resins according to the invention are noteworthy in that they are able to absorb and retain not only from 100 to 500 times their own weight of pure water but also from 20 to 60 times their weight of saline water, especially water containing monovalent or divalent salts of an alkali metal or alkaline earth metal such as, for example, sodium chloride, calcium chloride, potassium or sodium phosphate, potassium or magnesium sulphate, potassium or ammonium nitrate.

In addition, the Applicant has surprisingly found that the mechanical properties, especially the compressive strength, of the water-absorbing resins according to the invention may be very considerably improved when the said resins additionally comprise at least one cross-linking agent in a sufficient quantity, especially in a quantity of at least 1% by weight and preferably not exceeding 5% by weight based on the total of the monomers forming part of the said resins.

As a crosslinking agent, it is possible to use, for example:

(1) compounds containing at least two polymerizable double bonds, and (2) compounds containing at least one polymerizable double bond and at least one functional group reactive towards at least one of the monomers.

Examples of the compounds referred to firstly above, containing at least two polymerizable double bonds, are:

(a) di- or polyvinyl compounds such as, especially, divinylbenzene, divinyltoluene, divinylxylene, divinyl ether, divinyl ketone and trivinylbenzene, (b) di- or polyesters of unsaturated mono- or polycarboxylic acids with polyols, such as di- or triesters of (meth)acrylic acids with polyols (such as ethylene glycol, trimethylolpropane, glycerol, polyoxyethylene glycols, polyoxypropylene glycols, and the like), unsaturated polyesters (which may be obtained by the reaction of any one of the abovementioned polyols with an unsaturated acid such as maleic acid), di- or triesters of (meth)acrylic acid esters which may be obtained by the reaction of a polyepoxide with (meth)acrylic acid), (c) bis(meth)acrylamides such as N,N-methylenebisacrylamide, (d) carbamyl esters which may be obtained by reacting polyisocyanates (such as toluene diisocyanate, hexamethylene diisocyanate, 4,4'-diphenylmethane diisocyanate, and the like, and the prepolymers containing an NCO group which are obtained by reacting such a diisocyanate with compounds containing active hydrogen atoms) with monomers containing hydroxyl groups. Such esters are especially the di(meth)acrylates which may be obtained by reacting the abovementioned diisocyanates with hydroxyethyl (meth)acrylate, (e) di- or poly(meth)allyl ethers of polyols such as alkylene glycols, glycerol, polyalkylene glycols, polyoxyalkylenepolyols, carbohydrates, and the like), such as polyethylene glycol diallyl ether, allylated starch and allylated cellulose, (f) di- or polyallyl esters of polycarboxylic acids, such as diallyl phthalate, diallyl adipate, and the like, and (g) esters of unsaturated mono- or polycarboxylic acids with mono(meth)allyl ethers of polyols, such as the ester of (meth)acrylic acid with polyethylene glycol monoallyl ether.

The compounds of the type referred to secondly above, containing at least one polymerizable double bond and at least one functional group reactive towards at least one of the monomers, are ethylenically unsaturated compounds containing at least one group which reacts with carboxyl, carboxylic anhydride, hydroxyl, amino or amide groups. Examples of these compounds are N-methylol(meth)acrylamide, glycidyl (meth)acrylate, and the like.

The water-absorbing resins obtained in this manner have, furthermore, the considerable advantage, especially in applications in the field of agriculture, where they may be subjected to solar radiation, of retaining their water-absorbing and water-retaining properties after a prolonged exposure to ultraviolet radiation.

A second subject of the present invention consists of a process for the manufacture of the water-absorbing resins described above, by copolymerization of a mixture consisting of 40 to 60% on a molar basis of acrylic acid, at least partly in salt form if appropriate, and from 60 to 40% on a molar basis of at least one dialkylaminoalkyl acrylate, at least partially in salt form or quaternized if appropriate, in the presence of at least one free-radical generator, either in aqueous solution, for a period of between 1 and 240 minutes, at a temperature of between 2° and 98° C., or in an inverse emulsion, that is to say by dispersing the comonomers, mixed with water if appropriate, in an organic phase which is immiscible with water and with the monomers, in the presence of at least one emulsifying agent. This technique is generally referred to as polymerization in a "water-in-oil" emulsion. Examples of the organic phase are aliphatic hydrocarbons (pentane, hexane, heptane, decane, and the like, or mixtures thereof) or aromatic hydrocarbons (benzene, toluene, xylenes or mixtures thereof). The water/monomers weight ratio is generally less than or equal to 3. The weight ratio of the organic phase to the phase containing the monomers is preferably between 2 and 5. The emulsifying agents which can be used are lipophilic nonionic surface-active agents (mixed, if appropriate, with hydrophilic nonionic surface-active agents), such as, for example, sorbitan monooleate (by itself or mixed with ethoxylated sorbitan monooleate), sorbitan monostearate, or ethoxylated alkylphenols. The weight ratio of the emulsifying agent to the organic phase is preferably between 0.03 and 0.20. The reaction time is between 30 and 360 minutes, the reaction temperature is between 20° and 80° C.

In most cases the copolymerization will be carried out under atmospheric pressure. The polymerization temperature and time are chosen as a function of each other, the time being longer the lower the temperature, and vice versa. At the end of the recommended reaction time, the conversion of the mixture is generally very close to 100%. Any means capable of generating free radicals may be employed within the scope of the process according to the invention.

It may, in particular, involve microwaves, beta, gamma or untraviolet radiations, or chemical initiators. In the latter case, the polymerization initiator may be chosen, in particular, from persulphates, peroxides, hydroperoxides and diazo compounds; when an alkali metal persulphate is chosen, it may be used in combination with a reducing agent chosen from polyhydrophenols, sodium sulphite and bisulphite, dimethylaminopropionitrile, diazomercaptans and ferricyanides. The initiator and, if appropriate, the reducing agent may be used in a proportion of 0.1 to 2% of each by weight, based on the total monomers present. According to a particular embodiment of the invention, the polymerization may be performed using a noncontinuous process until the solids content of the mixture reaches approximately 20% by weight.

Lastly, a third subject of the present invention consists of articles capable of absorbing aqueous liquids, comprising at least one water-absorbing resin such as described earlier. Such articles may find various applications in the field of hygiene (babies' nappies and incontinence pads) because of their capacity for absorbing blood and/or urine, and in the field of agriculture (water retention in low-precipitation geographical regions) and in industry (dehydrating agents). They may be available, particularly, in powder or granular form.

The following examples are given by way of illustration of the present invention, without implying any limitation.

EXAMPLE 1

33.5 g of acrylic acid and 66.5 g of dimethylaminoethyl acrylate are dissolved in 400 g of water in the presence of a catalyst system comprising 1 g of ammonium persulphate and 1 g of sodium metabisulphite. Polymerization is then carried out at a temperature of 80° C. for 120 minutes. The resulting copolymer is then cooled and then dried for 24 hours in a ventilated oven at 60° C. and is finally dried under reduced pressure (100 mm Hg) at 30° C. After being ground to powder form, the product obtained is subjected to the following two tests:

Water absorption and retention capacity:

The product is gradually added with pure water or saline water containing 1% of sodium chloride until it is saturated. The weights of water which are absorbed to reach saturation are as follows:
pure water: 300 times the weight of copolymer;
saline water: 55 times the weight of copolymer.

Compressive strength:

1 g of powdered copolymer is swollen in 100 g of demineralized water. After centrifugal drying to remove all traces of unabsorbed water, the gel obtained is placed in a beaker with an internal diameter of 140 mm, in which it occupies a height of 50 mm. A 100 g weight is then placed on the gel, and the depth of penetration of this weight into the gel is then measured when it is stabilized. A depth of 40 mm is observed.

EXAMPLE 2

The procedures of Example 1 are repeated by polymerizing a mixture of 33 g of acrylic acid, 65.5 g of dimethylaminoethyl acrylate and 1.5 g of ethylene glycol dimethacrylate. In this case, the properties measured when the two tests described in Example 1 are carried out are as follows:

Water absorption and retention capacity:

pure water: 130 times the weight of copolymer;
saline water: 40 times the weight of copolymer.

Compressive strength:

Penetration depth: 10 mm

EXAMPLE 3

32.8 g of acrylic acid, 65.2 g of dimethylaminoethyl acrylate and 2 g of ethylene glycol dimethacrylate are dissolved in 400 g of water in the presence of 1 g of ammonium persulphate and 1 g of sodium metabisulphite. Polymerization is then carried out at a temperature of 85° C. for 180 minutes. The resulting copolymer, treated and ground as in Example 1, is subjected to the water absorption and retention test. The results are as follows:

pure water: 460 times the weight of copolymer;
saline water: 60 times the weight of copolymer.

Furthermore, the gel obtained after absorbing pure water to saturation is subjected for 1 hour to the ultraviolet radiation of a 4-watt lamp. After this treatment, the gel is centrifugal dried to remove all traces of unabsorbed water and is then weighed in order to measure its water retention capacity after aging. This is equal to 460 times.

EXAMPLE 4 (COMPARATIVE)

The procedures of Example 1 are repeated, with only the following exception: dimethylaminoethyl acrylate is replaced with dimethylaminoethyl methacrylate. The polymer obtained under these conditions is found to be incapable of absorbing pure water or saline water.

EXAMPLE 5 (COMPARATIVE)

The procedures of Example 1 are repeated, with only the following exception: acrylic acid is replaced with methacrylic acid. The polymer obtained under these conditions has the following absorption and retention capacities, measured using the test described in Example 1:

pure water: 60 times;
saline water: 15 times.

We claim:

1. Water-absorbing resin having a high capacity for absorbing and retaining pure or saline water
    comprising from 40 to 60% on a molar basis of acrylic acid and from 60 to 40% on a molar basis of at least one dialkylaminoalkyl acrylate in which each alkyl group contains from 1 to 4 carbon atoms.

2. Water-absorbing resin according to claim 1, further comprising at least one crosslinking agent in a quantity of between 1 and 5% by weight based on the total of the monomers.

3. Articles capable of absorbing aqueous liquids, comprising at least one water-absorbing resin according to claim 1.

4. Water absorbing resin according to claim 1 wherein said acrylic acid is partly replaced by at least one of its ammonium, alkali metal, or alkaline earth metal salts.

5. Water absorbing resin according to claim 1 wherein said dialkylaminoalkyl acrylate is partly replaced by at least one of its ammonium, quaternary ammonium, alkali metal, or alkaline earth metal salts.

6. Articles capable of absorbing aqueous liquids comprising at least one water-absorbing resin according to claim 2.

* * * * *